United States Patent
Yerkes et al.

(10) Patent No.: US 8,895,470 B2
(45) Date of Patent: Nov. 25, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND GLYPHOSATE OR GLUFOSINATE

(71) Applicant: Dow AgroSciences LLC, Indianapolis, IN (US)

(72) Inventors: Carla N. Yerkes, Crawfordsville, IN (US); Richard K. Mann, Franklin, IN (US); Paul R. Schmitzer, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/836,653

(22) Filed: Mar. 15, 2013

(65) Prior Publication Data
US 2014/0031227 A1    Jan. 30, 2014

Related U.S. Application Data

(60) Provisional application No. 61/675,083, filed on Jul. 24, 2012.

(51) Int. Cl.
*A01N 25/26* (2006.01)
*A01N 57/00* (2006.01)

(52) U.S. Cl.
USPC ........................................ 504/100; 504/128

(58) Field of Classification Search
None
See application file for complete search history.

(56) References Cited

U.S. PATENT DOCUMENTS

| | | | |
|---|---|---|---|
| 7,314,849 B2 * | 1/2008 | Balko et al. | 504/244 |
| 7,622,641 B2 | 11/2009 | McCutchen et al. | |
| 2009/0062121 A1 | 3/2009 | Satchivi et al. | |
| 2010/0137137 A1 | 6/2010 | Rosinger et al. | |
| 2011/0082162 A1 | 4/2011 | Lorsbach et al. | |
| 2011/0207607 A1 | 8/2011 | Satchivi et al. | |
| 2012/0115727 A1 | 5/2012 | Satchivi et al. | |
| 2012/0190551 A1 | 7/2012 | Yerkes et al. | |
| 2013/0109569 A1 | 5/2013 | Dave et al. | |
| 2013/0310256 A1 | 11/2013 | Yerkes et al. | |
| 2014/0031210 A1 | 1/2014 | Yerkes et al. | |
| 2014/0031211 A1 | 1/2014 | Yerkes et al. | |
| 2014/0031212 A1 | 1/2014 | Yerkes et al. | |
| 2014/0031213 A1 | 1/2014 | Yerkes et al. | |
| 2014/0031214 A1 | 1/2014 | Yerkes et al. | |
| 2014/0031215 A1 | 1/2014 | Yerkes et al. | |
| 2014/0031216 A1 | 1/2014 | Yerkes et al. | |
| 2014/0031217 A1 | 1/2014 | Yerkes et al. | |
| 2014/0031218 A1 | 1/2014 | Mann et al. | |
| 2014/0031219 A1 | 1/2014 | Yerkes et al. | |
| 2014/0031220 A1 | 1/2014 | Yerkes et al. | |
| 2014/0031221 A1 | 1/2014 | Yerkes et al. | |
| 2014/0031222 A1 | 1/2014 | Yerkes et al. | |
| 2014/0031228 A1 | 1/2014 | Mann et al. | |
| 2014/0031229 A1 | 1/2014 | Mann et al. | |

FOREIGN PATENT DOCUMENTS

WO    WO 2007/082098    7/2007

OTHER PUBLICATIONS

Thomas, S, Written Opinion of the International Search Authority for PCT/US2013/051318, Dec. 5, 2013, pp. 1-5, ISA/US.
Thomas, S, International Search Report for PCT/US2013/051318, Dec. 5, 2013, pp. 1-4, ISA/US.
Synthesis of Esters: Esterification Reactions, obtained via google. com, U.S. Appl. No. 13/840,306, obtained online Mar. 8, 2014.
Steglich Esterification, Organic Chemistry Portal, U.S. Appl. No. 13/840,306.
Chui, M.P., Non-Final Office Action in U.S. Appl. No. 13/840,306, Mar. 13, 2014, pp. 1- 12, USPTO.
Pryor, A.N., Notice of Allowance and Fee(s) Due for U.S. Appl. No. 13/832,978, Apr. 9, 2014, pp. 1-13, USPTO.
Pryor, A.N., Notice of Allowance and Fee(s) Due for U.S. Appl. No. 13/833,315, May 12, 2014, pp. 1-8, USPTO.
Pryor, A.N., Notice of Allowance and Fee(s) Due for U.S. Appl. No. 13/833,315, Mar. 20, 2014, pp. 1-11, USPTO.

(Continued)

*Primary Examiner* — Alton Pryor
(74) *Attorney, Agent, or Firm* — Michael R. Asam; Faegre Baker Daniels LLP

(57) ABSTRACT

Provided herein are synergistic herbicidal compositions containing and method for controlling undesirable vegetation utilizing (a) a compound of formula (I):

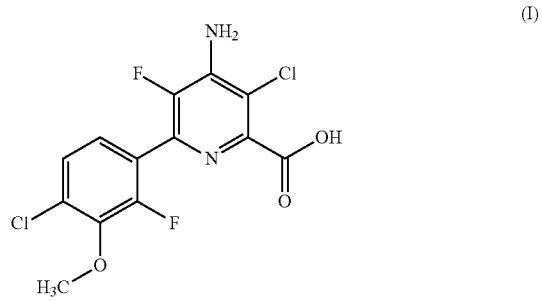

or an agriculturally acceptable salt or ester thereof and (b) glufosinate-ammonium, glyphosate dimethylammonium, glyphosate isopropylammonium, glyphosate trimesium, glufosinate or glyphosate, or an agriculturally acceptable derivative thereof. The methods and compositions herein provide control of undesirable vegetation, e.g., in direct-seeded, water-seeded and transplanted rice, cereals, wheat, barley, oats, rye, sorghum, corn or maize, sugarcane, sunflower, oilseed rape, canola, sugar beet, soybean, cotton, pineapple, vegetables, pastures, grasslands, rangelands, fallowland, turf, tree and vine orchards, plantation crops, aquatics, industrial vegetation management (IVM) or rights of way (ROW).

18 Claims, No Drawings

(56) References Cited

OTHER PUBLICATIONS

Pryor, A.N., Notice of Allowance and Fee(s) Due for U.S. Appl. No. 13/833,362, May 29, 2014, pp. 1-8, USPTO.
Pryor, A.N., Notice of Allowance and Fee(s) Due for U.S. Appl. No. 13/833,372, May 14, 2014, pp. 1-8, USPTO.
Pryor, A.N., Notice of Allowance and Fee(s) Due for U.S. Appl. No. 13/833,659, Mar. 17, 2014, pp. 1-12, USPTO.
Pryor, A.N., Notice of Allowance and Fee(s) Due for U.S. Appl. No. 13/833,923, May 2, 2014, pp. 1-9, USPTO.
Pryor, A.N., Notice of Allowance and Fee(s) Due for U.S. Appl. No. 13/833,965, Apr. 1, 2014, pp. 1-8, USPTO.
Pryor, A.N., Notice of Allowance and Fee(s) Due for U.S. Appl. No. 13/834,326, May 13, 2014, pp. 1-4, USPTO.
Pryor, A.N., Notice of Allowance and Fee(s) Due for U.S. Appl. No. 13/834,326, Apr. 2, 2014, pp. 1-9, USPTO.
Pryor, A.N., Notice of Allowance and Fee(s) Due for U.S. Appl. No. 13/834,706, Mar. 12, 2014, pp. 1-13, USPTO.
Pryor, A.N., Notice of Allowance and Fee(s) Due for U.S. Appl. No. 13/837,990, Apr. 1, 2014, pp. 1-8, USPTO.
Pryor, A.N., Notice of Allowance and Fee(s) Due for U.S. Appl. No. 13/839,043, May 27, 2014, pp. 1-5, USPTO.
Pryor, A.N., Notice of Allowance and Fee(s) Due for U.S. Appl. No. 13/839,043, Mar. 24, 2014, pp. 1-8, USPTO.
Pryor, A.N., Notice of Allowance and Fee(s) Due for U.S. Appl. No. 13/840,236, Apr. 25, 2014, pp. 1-8, USPTO.
Pryor, A.N., Notice of Allowance and Fee(s) Due for U.S. Appl. No. 13/840,303, Apr. 25, 2014, pp. 1-8, USPTO.
Pryor, A.N., Notice of Allowance and Fee(s) Due for U.S. Appl. No. 13/840,346, Jun. 4, 2014, pp. 1-8, USPTO.
Pryor, A.N., Notice of Allowance and Fee(s) Due for U.S. Appl. No. 13/840,419, May 5, 2014, pp. 1-8, USPTO.
Pryor, A.N., Notice of Allowance and Fee(s) Due for U.S. Appl. No. 13/840,488, May 2, 2014, pp. 1-8, USPTO.

* cited by examiner

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND GLYPHOSATE OR GLUFOSINATE

PRIORITY CLAIM

This application claims the benefit of U.S. provisional patent application No. 61/675,083 filed on Jul. 24, 2012, this provisional application is incorporated herein by reference in its entirety.

FIELD

Provided herein are herbicidal compositions comprising and methods for controlling undesirable vegetation utilizing (a) 4-amino-3-chloro-5-fluoro-6-(4-chloro-2-fluoro-3-methoxyphenyl)pyridine-2-carboxylic acid or an agriculturally acceptable ester or salt thereof and (b) glyphosate or glufosinate or an agriculturally acceptable salt thereof.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment of the invention provided herein includes herbicidal compositions comprising an herbicidally effective amount of (a) a compound of the formula (I)

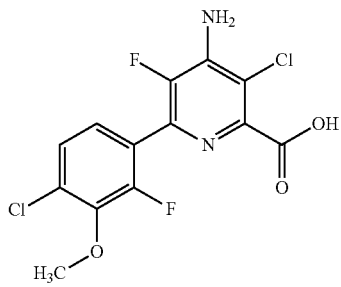

(I)

or an agriculturally acceptable salt or ester thereof, and (b) selected from the group consisting of glyphosate and glufosinate or an agriculturally acceptable salt thereof.

A second embodiment includes the mixture of the first embodiment in which of formula (I), is present in the form of at least one of the following forms: a carboxylic acid, a carboxylate salt, an aralkyl, an alkyl ester, an unsubstituted benzyl, a substituted benzyl, a $C_{1-4}$ alkyl, and/or an n-butyl ester.

A third embodiment includes the mixtures according to any of the first, or second, embodiments in which (b) is glyphosate or an agriculturally acceptable salt thereof wherein the weight ratio of the compound of formula (I) to glyphosate or its salt is given in units of gae/ha to gai/ha or gae/ha to gae/ha is selected from the group of ranges of ratios and ratios consisting of, about: 1:1120 to 3:1, 1:852 to 10:1, 1:29, 1:14, 1:57, 1:7, 1:24, 1:12, 1:48, 1:6, 1:96, 1:19, 1:26, 1:13, 1:28, 1:56, 1:105, 1:52.5, 1:210, 1:7, 1:112, 1:420, 1:800, or within any range defined between any pair of the foregoing values.

A fourth embodiment includes the mixtures according to any of the first or second, embodiments in which (b) is glufosinate or an agriculturally acceptable salt thereof wherein the weight ratio of the compound of formula (I) to glufosinate or its salt is in units of gae/ha to gai/ha or gae/ha to gae/ha is selected from the group of ranges of ratios and ratios consisting of, about: 1:780 to 11:1, 1:31, 1:15.5, 11:1, 1:62, 1:7.7, 1:39, 1:14, 1:7, 1:3.5, 1:3.8, 1:1.9, 1:7.5, 1:72, 1:36, 1:18, 1:145, 1:72.3, 1:36, 1:112, 1:56, 1:112.5, 1:28, 1:7, 1:225, or within any range defined between any pair of the foregoing values.

A fifth embodiment includes any composition according to any of the first through the fourth embodiments wherein the mixture further comprises at least one agriculturally acceptable agent selected from the group consisting of an adjuvant, a carrier, or a safener.

A sixth embodiment includes methods of controlling undesirable vegetation comprising the step of applying or otherwise contacting vegetation and/or soil, and/or water with a herbicidally effective amount of at least one mixture according to any of the first through the fifth embodiments.

An seventh embodiment includes methods according to the sixth embodiment wherein undesirable vegetation is controlled according to at least technique selected from the group consisting of: direct-seeded, water-seeded, and/or transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM), or rights-of-way (ROW).

An eighth embodiment includes methods according to either of the sixth and the seventh embodiments wherein a herbicidally effective amount of the mixture is applied either pre- or post emergently to at least one of the following: a crop, a field, a ROW, or a paddy.

A ninth embodiment includes methods according to any of the sixth through the eighth embodiments wherein the undesirable vegetation controlled by an application of a herbicidally effective amount of the mixture and at least one of the following phytotoxic actives: glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS)inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase (PPO) inhibitor-, triazine-, or bromoxynil-tolerant crops.

A tenth embodiment includes a at least one method according to any of the sixth through the ninth embodiments wherein a plant that is tolerant to at least one herbicide is treated, and where the tolerant crop possesses multiple or stacked traits conferring tolerance to multiple herbicides or inhibitors of multiple modes of action, in some embodiments the treated plant that expresses resistance to a herbicide is a itself undesirable vegetation.

An eleventh embodiment includes methods according to the tenth embodiment, wherein the resistant or tolerant weed is a biotype with resistance or tolerance to multiple herbicides, multiple chemical classes, inhibitors of multiple herbicide modes-of-action, or via multiple resistance mechanisms.

A twelfth embodiment includes at least one of the methods according to either the tenth or the eleventh embodiments, wherein the resistant or tolerant undesirable plant is a biotype resistant or tolerant to at least on agent selected from the groups consisting of: acetolactate synthase (ALS) inhibitors or acetohydroxy acid synthase (AHAS), photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

A thirteenth embodiment includes methods of controlling undesirable vegetation comprising the step of applying a herbicidally effective amount of at least one mixture according to the third embodiment wherein the amount of the mixture is applied at a rate, expressed in gai/ha or gae/ha of glyposate or a salt of glyposate selected from the group of rates and ranges of rates consisting of, about: 124.5, 249, 105, 210, 420, 377, 25, 50, 75, 100, or within any range defined between any pair of the foregoing values.

A fourteenth embodiment includes methods according to either of the third and thirteenth embodiments wherein the controlled plant is at least one plant selected from the group consisting of: ECHCG, ECHCO, LEFCH, CYPDI, IPOHE, DIGSA, ECHCG, SCPMA, SORHA, VIOTR, SETFA, CHEAL and CYPES and still other embodiments include controlling plants from the genera consisting of *Echinochloa, Leptochloa, Cyperus, Ipomoea, Digitaria, Echinochloa, Schoenoplectus, Viola, Setaria, Chenopodium*, and *Cyperus*.

A fifteenth embodiment includes methods of controlling undesirable vegetation comprising the step of applying a herbicidally effective amount of at least one a mixture according to the fourth embodiment wherein the amount of the mixture is applied at a rate, expressed in gai/ha or gae/ha of glufosinate or an agriculturally acceptable salt thereof selected from the group of rates and ranges of rates consisting of, about: 25, 28.3, 56.5, 113, 271, 542, 135.5, 112.5, 225, 450, or within any range defined between any pair of the foregoing values.

A sixteenth embodiment includes methods according to either of the fourth and fifteenth embodiments wherein the controlled plant is at least one plant selected from the group consisting of: DIGSA, ECHCG, ECHCO, CYPDI, LEFCH, IPOHE, AVEFA, ELEIN, SORHA, CIRAR, AMARE, CHEAL, CYPES, and SETFA, still other embodiments include controlling plants from the genera consisting of: *Digitaria, Echinochloa, Leptochloa, Ipomoea, Avena, Eleusine, Sorghum, Cirsium, Amaranthus, Chenopodium, Cyperus*, and *Setaria*.

Provided herein are herbicidal compositions comprising a herbicidally effective amount of (a) a compound of the formula (I)

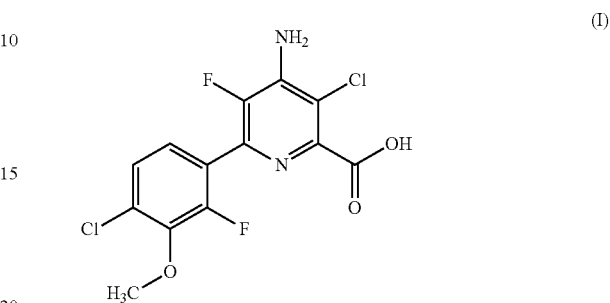

or an agriculturally acceptable salt or ester of thereof, and (b) glyphosate or glufosinate or an agriculturally acceptable salt and ester thereof. The compositions may also contain an agriculturally acceptable adjuvant or carrier.

Provided herein are also methods of controlling undesirable vegetation comprising applying (a) a compound of formula (I) or an agriculturally acceptable ester or salt thereof and (b) glyphosate or glufosinate or an agriculturally acceptable salt or ester thereof.

DETAILED DESCRIPTION

Definitions

As used herein, the compound of formula (I) has the following structure:

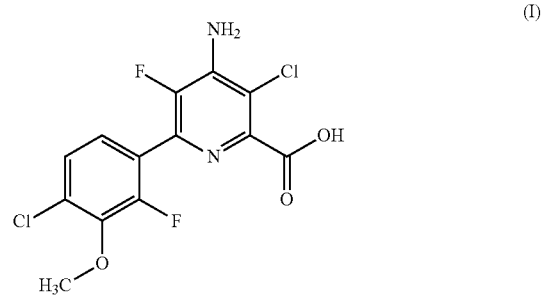 [SMILES: COc1c(Cl)ccc(-c2nc(C(=O)O)c(Cl)c(N)c2F)c1F]

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Glufosinate is 2-amino-4-[hydroxy(methyl)phophinoyl] butyic acid. An exemplary form of glufosinate is glufosinate-ammonium, the ammonium salt of glufosinate. It can be referred to as 2-amino-4-(hydroxymethylphosphinyl)butanoic acid monoammonium salt and possesses the following structure:

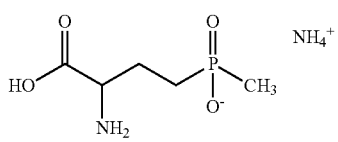

Other chemical forms of glufosinate (or phosphinothricin) include bialaphos, which is 2-amino-4-(methylphosphino) butyrylalanylalanine and possesses the following structure:

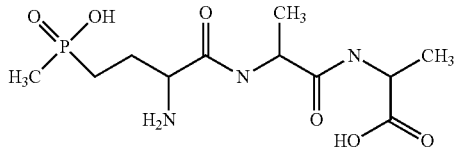 [SMILES: CC(NC(=O)C(C)NC(=O)C(N)CCP(C)(=O)O)C(=O)O]

Bialaphos also can be used in the salt form such as bialaphos sodium. Exemplary uses are described in Tomlin, C., and ed. A World Compendium The Pesticide Manual. 15<sup>th</sup> ed. Alton: BCPC Publications, 2009 (hereafter "*The Pesticide Manual*, Fifteenth Edition, 2009."). Exemplary uses include its use to control annual and perennial broadleaf weeds and grasses. Other chemical forms include glufosinate-P, i.e., S-2-amino-4-[hydroxy(methyl)phophinoyl]butyric acid.

As used herein, glyphosate is N-(phosphonomethyl)glycine and possesses the following structure:

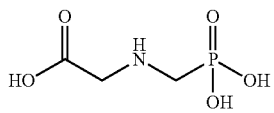

Exemplary uses of glyphosate are described in *The Pesticide Manual*, Fifteenth Edition, 2009. Exemplary uses of glyphosate include its use for control of annual and perennial grasses and broadleaf weeds. Other forms of glyphosate include its dimethylammonium salt, dimethylamino salt, isopropyl ammonium salt, trimesium salt (sulfosate), monoammonium salt, diammonium salt, potassium salt, and sesquisodium salt.

As used herein, herbicide means a compound, e.g., active ingredient that kills, controls or otherwise adversely modifies the growth of plants.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines Exemplary cations include sodium, potassium, magnesium, and aminium cations of the formula:

$R^1R^2R^3R^4N^+$ wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

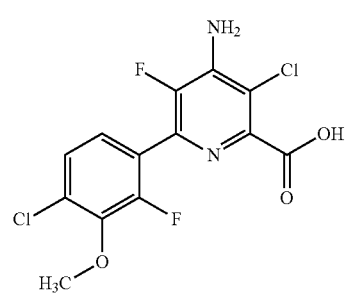

(I)

or an agriculturally acceptable salt or ester of thereof, and (b) glufosinate or glyphosate, or agriculturally acceptable salts or esters thereof.

Provided herein are also methods of controlling undesirable vegetation comprising contacting the vegetation or the locus thereof, i.e., area adjacent to the vegetation, with or applying to the soil or water to prevent the emergence or growth of vegetation a herbicidally effective amount of the compound of formula (I) or agriculturally acceptable salt or ester thereof and (b) glufosinate or glyphosate, or agriculturally acceptable salts or esters thereof. In certain embodiments, the methods employ the compositions described herein.

Furthermore, in some embodiments, the combination of compound (I) or an agriculturally acceptable salt or ester thereof and glyphosate or glufosinate herbicides, or an agriculturally acceptable salt or ester thereof, exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed. Herbicide Handbook. $9^{th}$ ed. Lawrence: Weed Science Society of America, 2007. In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and glufosinate or glyphosate or an agriculturally acceptable salt thereof are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, plantation crops, vegetables, aquatics, industrial vegetation management (IVM) and rights of way ROW).

In certain embodiments, the compositions and methods provided herein are utilized to control weeds in rice. In certain embodiments, the rice is direct-seeded, water-seeded, or transplanted rice.

The compositions and methods described herein may be used to control undesirable vegetation in glyphosate-tolerant-, 5-enolpyruvylshikimate-3-phosphate (EPSP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant-, and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

The compositions and methods provided herein are utilized to control undesirable vegetation. Undesirable vegetation includes, but is not limited to, undesirable vegetation that occurs in direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, plantation crops, vegetables, aquatics, industrial vegetation management (IVM) and rights of way ROW). In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schuh. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (tidalmarsh flatsedge, CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* POIR. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Berm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R.D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp.

*Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kyllinga* species (*kyllinga*, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhorn/narrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS). In some embodiments, the compositions and methods provided herein are utilized to control undesirable vegetation consisting of grass, broadleaf and sedge weeds. In certain embodiments, the compositions and methods provided herein are utilized to control undesirable vegetation including *Amaranthus, Avena, Chenopodium, Cirsium, Cyperus, Digitaria, Echinochloa, Eleusine, Ipomoea, Leptochloa, Setaria, Bolboschoenus* or *Schoenoplectus, Sorghum* and *Viola.*

In some embodiments, the combination of compound (I) or agriculturally acceptable ester or salt thereof and glyphosate or glufosinate, or agriculturally acceptable salt or ester thereof, is used to control *Amaranthus retroflexus* L. (redroot pigweed, AMARE), *Avena fatua* L. (wild oat, AVEFA), *Chenopodium album* L. (common lambsquarters, CHEAL), *Cirsium arvense* (L.) Scop (Canada thistle, CIRAR), *Cyperus difformis* L. (smallflower umbrella sedge, CYPDI), *Cyperus esculentus* L. (yellow nutsedge, CYPES), *Digitaria sanguinalis* (L.) Scop. (large crabgrass, DIGSA), *Echinochloa crus-galli* (L.) Beauv. (barnyardgrass, ECHCG), *Echinochloa colona* (L.) Link (junglerice, ECHCO), *Eleusine indica* (L.) Gaertn. (goosegrass, ELEIN), *Ipomoea hederacea* Jacq. (ivyleaf morningglory, IPOHE), *Leptochloa chinensis* (L.) Nees (Chinese sprangletop, LEFCH), *Schoenoplectus maritimus* (L.) Lye or *Bolboschoenus maritimus* (L.) Palla (sea clubrush, SCPMA), *Setaria faberi* Herrm. (giant foxtail, SETFA), *Sorghum halepense* (L.) Pers. (johnsongrass, SORHA) and *Viola tricolor* L. (pansy, VIOTR).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors, (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

In certain embodiments of the compositions and methods described herein, the compound of formula (I) or salt or ester thereof is used in combination with glufosinate-ammonium or salt or carboxylic acid thereof. With respect to the compositions, in some embodiments, the weight ratio of the compound of formula I to glufosinate-ammonium or salt or carboxylic acid thereof is from about 1:1 to about 1:300. In some embodiments, the weight ratio of the compound of formula I to glufosinate-ammonium or salt or carboxylic acid thereof is from about 1:2 to about 1:145. In certain embodiments, the compositions provided herein comprise the compound of formula (I) or its benzyl ester and glufosinate-ammonium. In some embodiments, the weight ratio of the compound of formula (I) or benzyl ester thereof to glufosinate-ammonium is within the range of from about 1:780 to about 11:1. In certain embodiments, the weight ratio of the compound of formula (I) or benzyl ester thereof to glufosinate-ammonium is within the range of from about 1:123 to about 1:2. In one embodiment, the composition comprises the compound of formula I and glufosinate-ammonium, wherein the weight ration of the compound of formula I to glufosinate-ammonium is from about 1:2 to about 1:145. In one embodiment, the composition comprises the benzyl ester of the compound of formula I and glufosinate-ammonium, wherein the weight ratio of the benzyl ester of the compound of formula I to glufosinate-ammonium is from about 1:16 to about 1:145. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 30 grams acid equivalent per hectare (gae/ha) to about 1860 gae/ha based on the total amount of active ingredients in the composition. In certain embodiments, the composition is applied at an application rate of from about 32 grams acid equivalent per hectare (gae/ha) to about 565 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and glufosinate or salt thereof, e.g., sequentially or simultaneously. In some embodiments, the glufosinate-ammonium or salt or carboxylic acid thereof is applied at a rate from about 28 gae/ha to about 1560 gae/ha and the compound of formula (I) of salt or ester thereof is applied at a rate from about 2 gae/ha to about 300 gae/ha. In some embodiments, the glufosinate-ammonium or salt or carboxylic acid thereof is applied at a rate from about 14 gae/ha to about 1000 gae/ha and the compound of formula (I) of salt or ester thereof is applied at a rate from about 1.5 g acid equivalent per hectare (gae/ha) to about 40 gae/ha. In some embodiments, the glufosinate-ammonium or salt or carboxylic acid thereof is applied at a rate from about 28 gae/ha to about 545 gae/ha and the compound of formula (I) of salt or ester thereof is applied at a rate from about 3 g acid equivalent per hectare (gae/ha) to about 32 gae/ha. In certain embodiments, the methods utilize the compound of formula (I) or its benzyl ester and glufosinate-ammonium. In one embodiment, the methods utilize the benzyl ester of the compound of formula (I) and glufosinate-ammonium, wherein the benzyl ester of the compound of formula (I) is applied at a rate of from about 4 to about 40 gae/ha, and the glufosinate ammonium is applied at a rate of from about 130 to about 545 gae/ha. In one embodiment, the methods utilize the compound of formula (I) and glufosinate-ammonium, wherein the compound of formula (I) is applied at a rate of from about 3 to about 18 gae/ha, and the glufosinate-ammonium is applied at a rate of from about 28 to about 545 gae/ha. In certain embodiments, the methods and compositions utilizing the compound of formula (I) or salt or ester thereof in combination with glufosinate-ammonium or salt or carboxylic acid thereof are used to control SORHA, DIGSA, EGHCG, ECHCO, CYPDI, LEFCH, ELEIN, AVEFA, IPOHE, CIRAR, AMARE, CHEAL, CYPES or SETFA.

In certain embodiments of the compositions and methods described herein, the compound of formula (I) or salt or ester thereof is used in combination with glufosinate-ammonium or salt thereof. With respect to the compositions, in some embodiments, the weight ratio of the compound of formula I to glufosinate-ammonium or salt thereof is from about 1:780 to about 11:1. In certain embodiments, the compositions provided herein comprise the compound of formula (I) or its benzyl ester and glufosinate-ammonium. In some embodiments, the weight ratio of the compound of formula (I) or benzyl ester thereof to glufosinate-ammonium is within the range of from about 1:780 to about 11:1. In certain embodiments, the weight ratio of the compound of formula (I) or benzyl ester thereof to glufosinate-ammonium is within the range of from about 1:271 to about 1:1. In one embodiment, the composition comprises the compound of formula I and glufosinate-ammonium, wherein the weight ration of the compound of formula I to glufosinate-ammonium is from about 1:2 to about 1:145. In one embodiment, the composition comprises the benzyl ester of the compound of formula I and glufosinate-ammonium, wherein the weight ratio of the benzyl ester of the compound of formula I to glufosinate-ammonium is from about 1:16 to about 1:145. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 30 grams acid equivalent per hectare (gae/ha) to about 1860 gae/ha based on the total amount of active ingredients in the composition. In certain embodiments, the composition is applied at an application rate of from about 31 grams acid equivalent per hectare (gae/ha) to about 574 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and glufosinate or salt thereof, e.g., sequentially or simultaneously. In some embodiments, the glufosinate-ammonium or salt thereof is applied at a rate from about 28 gae/ha to about 1560 gae/ha and the compound of formula (I) of salt or ester thereof is applied at a rate from about 2 gae/ha to about 300 gae/ha. In some embodiments, the glufosinate-ammonium or salt thereof is applied at a rate from about 14 gae/ha to about 1120 gae/ha and the compound of formula (I) of salt or ester thereof is applied at a rate from about 1.5 g acid equivalent per hectare (gae/ha) to about 100 gae/ha. In some embodiments, the glufosinate-ammonium or salt thereof is applied at a rate from about 28 gae/ha to about 542 gae/ha and the compound of formula (I) of salt or ester thereof is applied at a rate from about 2 g acid equivalent per hectare (gae/ha) to about 32 gae/ha. In certain embodiments, the methods utilize the compound of formula (I) or its benzyl ester and glufosinate-ammonium. In one embodiment, the methods utilize the benzyl ester of the compound of formula (I) and glufosinate-ammonium, wherein the benzyl ester of the compound of formula (I) is applied at a rate of from about 4 to about 60 gae/ha, and the glufosinate-ammonium is applied at a rate of from about 30 to about 545 gae/ha. In one embodiment, the methods utilize the compound of formula (I) and glufosinate-ammonium, wherein the compound of formula (I) is applied at a rate of from about 2 to about 32 gae/ha, and the glufosinate-ammonium is applied at a rate of from about 28 to about 542 gae/ha. In certain embodiments, the methods and compositions utilizing the compound of formula (I) or salt or ester thereof in combination with glufosinate-ammonium or salt thereof are used to control SORHA, DIGSA, EGHCG, ECHCO, CYPDI, LEFCH, ELEIN, AVEFA, IPOHE, CIRAR, AMARE, CHEAL, CYPES or SETFA.

In certain embodiments of the compositions and methods described herein, the compound of formula (I) or salt or ester thereof is used in combination with glyphosate or salt thereof. In some embodiments, the weight ratio of the compound of formula (I) or salt or ester thereof to glyphosate or salt thereof is within the range of from about 1:1120 to about 3:1. In certain embodiments, the weight ratio of the compound of formula (I) or salt or ester thereof to glyphosate or salt thereof is within the range of from 1:95 to about 1:3. In some embodiments, the weight ratio of the compound of formula I or salt or ester thereof and glyphosate or salt thereof is from about 1:3 to about 1:220. In some embodiments, the weight ratio of the compound of formula I or salt or ester thereof and glyphosate or salt thereof is from about 1:6 to about 1:112. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 107 grams acid equivalent per hectare (gae/ha) to about 2540 gae/ha based on the total amount of active ingredients in the composition. In certain embodiments, the composition is applied at an application rate of from about 109 grams acid equivalent per hectare (gae/ha) to about 450 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and glyphosate or salt thereof, e.g., sequentially or simultaneously. In some embodiments, the glyphosate or salt or ester thereof is applied at a rate from about 30 gae/ha to about 2240 gae/ha and the compound of formula (I) of salt or ester thereof is applied at a rate from about 2 gae/ha to about 300 gae/ha. In some embodiments, the application rate of the compound of formula I or salt or ester thereof is from about 2 gae/ha to about 70 gae/ha, and the application rate of the glyphosate or salt thereof is from about 100 to about 1000 gai/ha. In some embodiments, the application rate of the compound of formula I or salt or ester thereof is from about 4.38 gae/ha to about 35 gae/ha, and the application rate of the glyphosate or salt thereof is from about 200 to about 500 gai/ha. In certain embodiments, the methods and compositions utilizing the compound of formula (I) or salt or ester thereof in combination with glyphosate or salt thereof are used to control ECHCG, ECHCO, LEFCH, CYPDI, SCPMA, IPOHE, DIGSA, or SORHA.

In certain embodiments, glyphosate dimethylammonium (DMA) salt is utilized. In some embodiments, the weight ratio of the compound of formula (I) or salt or ester thereof to glyphosate dimethylammonium or salt or ester thereof is within the range of from about 1:1120 to about 2:1. In certain embodiments, the weight ratio of the compound of formula (I) or salt or ester thereof to glyphosate dimethylammonium or salt or ester thereof is within the range of from 1:25 to about 1:10. In certain embodiments, the weight ratio of the compound of formula (I) or salt or ester thereof to glyphosate dimethylammonium is from 1:10 to about 1:220 In certain embodiments, the weight ratio of the compound of formula (I) or salt or ester thereof to glyphosate dimethylammonium is from about 1:22 to about 1:112. In some embodiments, the composition comprises the compound of formula I and glyphosate dimethylammonium. In some embodiments, the composition comprises the compound of formula I and glyphosate dimethylammonium, wherein the weight ratio of the compound of formula I to glyphosate dimethylammonium is from about 1:22 to about 1:112. In some embodiments, the composition comprises the n-butyl ester of the compound of formula I and glyphosate dimethylammonium. In some embodiments, the composition comprises the n-butyl ester of the compound of formula I and glyphosate dimethylammonium, wherein the weight ratio of the compound of formula I to glyphosate dimethylammonium is about 1:26. In some embodiments, the composition comprises the benzyl ester of the compound of formula I and glyphosate dimethylammonium. In some embodiments, the composition comprises the benzyl ester of the compound of formula I and glyphosate dimethylammonium, wherein the weight ratio of the compound of formula I to glyphosate dimethylammonium is about 1:26. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 160 grams acid equivalent per hectare (gae/ha) to about 2540 gae/ha based on the total amount of active ingredients in the composition. In certain embodiments, the composition is applied at an application rate of from about 400 grams acid equivalent per hectare (gae/ha) to about 460 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and glyphosate dimethylammonium, e.g., sequentially or simultaneously. In certain embodiments, the methods utilize the compound of formula I and glyphosate dimethylammonium, wherein the compound of formula I is applied at an application rate of from about 3 to about 20 gae/ha, and the glyphosate dimethylammonium is applied at a rate of from about 200 to about 450 gai/ha. In certain embodiments, the methods utilize the n-butyl ester or benzyl ester of the compound of formula I and glyphosate dimethylammonium, wherein the n-butyl ester or benzyl ester of the compound of formula I is applied at an application rate of about 16 gae/ha, and the glyphosate dimethylammonium is applied at a rate of about 420 gai/ha. In some embodiments, the glyphosate is applied at a rate from about 160 gae/ha to about 2240 gae/ha and the compound of formula (I) of salt or ester thereof is applied at a rate from about 2 gae/ha to about 300 gae/ha. In certain embodiments, the methods and compositions utilizing the compound of formula (I) or salt or ester thereof in combination with glyphosate dimethyl ammonium are used to control CYPES, DIGSA, ECHCG, LEFCH, SETFA, SORHA, and VIOTR.

In certain embodiments, glyphosate dimethylammonium (DMA) salt is utilized. In some embodiments, the weight ratio of the compound of formula (I) or salt or ester thereof to glyphosate dimethylammonium or salt or ester thereof is within the range of from about 1:1120 to about 3:1. In certain embodiments, the weight ratio of the compound of formula (I) or salt or ester thereof to glyphosate dimethylammonium or salt or ester thereof is within the range of from 1:420 to about 1:4. In certain embodiments, the weight ratio of the compound of formula (I) or salt or ester thereof to glyphosate dimethylammonium is from 1:10 to about 1:220 In certain embodiments, the weight ratio of the compound of formula (I) or salt or ester thereof to glyphosate dimethylammonium is from about 1:22 to about 1:112. In some embodiments, the composition comprises the compound of formula I and glyphosate dimethylammonium. In some embodiments, the composition comprises the compound of formula I and glyphosate dimethylammonium, wherein the weight ratio of the compound of formula I to glyphosate dimethylammonium is from about 1:22 to about 1:112. In some embodiments, the composition comprises the n-butyl ester of the compound of formula I and glyphosate dimethylammonium. In some embodiments, the composition comprises the n-butyl ester of the compound of formula I and glyphosate dimethylammonium, wherein the weight ratio of the compound of formula I to glyphosate dimethylammonium is about 1:26. In some embodiments, the composition comprises the benzyl ester of the compound of formula I and glyphosate dimethylammonium. In some embodiments, the composition comprises the benzyl ester of the compound of formula I and glyphosate dimethylammonium, wherein the weight ratio of the compound of formula I to glyphosate dimethylammonium is about 1:26. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 75 grams acid equivalent per hectare (gae/ha) to about 2540 gae/ha based on the total amount of active ingredients in the composition. In certain embodiments, the composition is applied at an application rate of from about 102 grams acid equivalent per hectare (gae/ha) to about 872 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and glyphosate dimethylammonium, e.g., sequentially or simultaneously. In certain embodiments, the methods utilize the compound of formula I and glyphosate dimethylammonium, wherein the compound of formula I is applied at an application rate of from about 3 to about 32 gae/ha, and the glyphosate dimethylammonium is applied at a rate of from about 105 to about 840 gai/ha. In certain embodiments, the methods utilize the n-butyl ester or benzyl ester of the compound of formula I and glyphosate dimethylammonium, wherein the n-butyl ester or benzyl ester of the compound of formula I is applied at an application rate of about 32 gae/ha, and the glyphosate dimethylammonium is applied at a rate of about 840 gai/ha. In some embodiments, the glyphosate is applied at a rate from about 105 gai/ha to about 2240 gai/ha and the compound of formula (I) of salt or ester thereof is applied at a rate from about 2 gae/ha to about 300 gae/ha. In certain embodiments, the methods and compositions utilizing the compound of formula (I) or salt or ester thereof in combination with glyphosate dimethyl ammonium are used to control CYPES, DIGSA, ECHCG, LEFCH, SETFA, SORHA, and VIOTR.

In certain embodiments, glyphosate isopropylammonium (IPA) salt is utilized. In some embodiments, the weight ratio of the compound of formula (I) or salt or ester thereof to glyphosate isopropylammonium is within the range of from about 1:1120 to about 3:1. In certain embodiments, the weight ratio of the compound of formula (I) or salt or ester thereof to glyphosate isopropylammonium is within the range of from 1:95 to about 1:6. In some embodiments, the weight ratio of the compound of formula I or salt or ester thereof to glyphosate isopropylammonium is from about 1:3 to about 1:200. In some embodiments, the weight ratio of the compound of formula I or salt or ester thereof to glyphosate isopropylammonium is from about 1:6 to about 1:96. In some embodiments, the composition comprises the compound of formula I and glyphosate isopropylammonium. In certain embodiments, the weight ratio of the compound of formula I to glyphosate isopropylammonium is from about 1:6 to about 1:96. In some embodiments, the composition comprises the benzyl ester of the compound of formula I and glyphosate isopropylammonium. In certain embodiments, the weight ratio of the benzyl ester of the compound of formula I to glyphosate isopropylammonium is from about 1:6 to about 1:48. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 107 grams acid equivalent per hectare (gae/ha) to about 2540 gae/ha based on the total amount of active ingredients in the composition. In certain embodiments, the composition is applied at an application rate of from about 109 grams acid equivalent per hectare (gae/ha) to about 450 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and glyphosate isopropylammonium, e.g., sequentially or simultaneously.

In some embodiments, the glyphosate isopropylammonium is applied at a rate from about 105 gae/ha to about 2240 gae/ha and the compound of formula (I) of salt or ester thereof is applied at a rate from about 2 gae/ha to about 300 gae/ha. In certain embodiments, the glyphosate isopropylammonium is applied at a rate from about 50 gae/ha to about 800 gae/ha and the compound of formula (I) of salt or ester thereof is applied at a rate from about 2 gae/ha to about 70 gae/ha. In certain embodiments, the glyphosate isopropylammonium is applied at a rate from about 105 gae/ha to about 420 gae/ha and the compound of formula (I) of salt or ester thereof is applied at a rate from about 4 gae/ha to about 35 gae/ha. In certain embodiments, the methods utilize the compound of formula I and glyphosate isopropylammonium, wherein the compound of formula I is applied at an application rate of from about 4 to about 35 gae/ha, and the glyphosate isopropylammonium is applied at a rate of from about 100 to about 420 gai/ha. In certain embodiments, the methods utilize the benzyl ester of the compound of formula I and glyphosate isopropylammonium, wherein the benzyl ester of the compound of formula I is applied at an application rate of from about 4 g to about 35 ae/ha, and the glyphosate isopropylammonium is applied at a rate of about 100 to about 450 gai/ha. In certain embodiments, the methods and compositions utilizing the compound of formula (I) or salt or ester thereof in combination with glyphosate dimethyl ammonium are used to control ECHCG, ECHCO, LEFCH, CYPDI, SCPMA, or IPOHE.

In certain embodiments of the compositions and methods described herein, the compound of formula (I) or salt or ester thereof is used in combination with glyphosate trimesium (also known as sulfosate). In some embodiments, the weight ratio of the compound of formula (I) or salt or ester thereof to glyphosate trimesium is within the range of from about 1:852 to about 10:1. In certain embodiments, the weight ratio of the compound of formula (I) or salt or ester thereof to glyphosate trimesium is within the range of from 1:136 to about 1:1. In some embodiments, the composition is applied at an application rate of from about 30 grams acid equivalent per hectare (gae/ha) to about 2000 gae/ha based on the total amount of active ingredients in the composition. In certain embodiments, the composition is applied at an application rate of from about 35 grams acid equivalent per hectare (gae/ha) to about 650 gae/ha based on the total amount of active ingredients in the composition. In some embodiments, the glyphosate trimesium is applied at a rate from about 30 gae/ha to about 1705 gae/ha and the compound of formula (I) of salt or ester thereof is applied at a rate from about 2 gae/ha to about 300 gae/ha.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialophos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenterecol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, fluroxypyr-meptyl, flurtamone, fluthiacet, fomesafen, foramsulfuron, fosamine, fumiclorac, furyloxyfen, halauxifen, halauxifen-methyl, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, SYN-523, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

In some embodiments, the compositions described herein are employed in combination with one or more herbicide safeners, such as AD-67 (MON 4660), benoxacor, benthiocarb, brassinolide, cloquintocet(mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, 829148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet(mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, ethephon, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, tree and vine orchards, plantation crops, vegetables, and non-crop (ornamentals) settings. In some embodiments, the plant growth regulator is mixed with the compound of formula (I), or mixed with the compound of formula (I) and glyphosate or glufosinate to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, Water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiment's about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 15.0 weight percent active ingredient and in certain embodiments contain about 0.01 to 10.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I, II, III, and IV are greenhouse trial results.

Example I

Evaluation of Postemergence Foliar-Applied Herbicidal Mixtures for Weed Control in Direct Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 hr photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC (suspension concentrate), and various herbicidal components alone and in combination. Forms of compound A were applied on an acid equivalent basis.

Forms of compound A (compound of formula I) tested include:

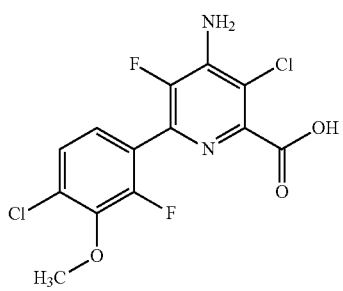

Compound A
Acid

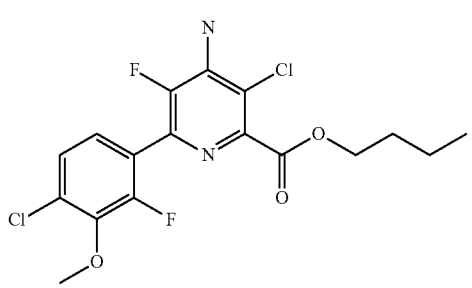

Compound A
n-Butyl Ester

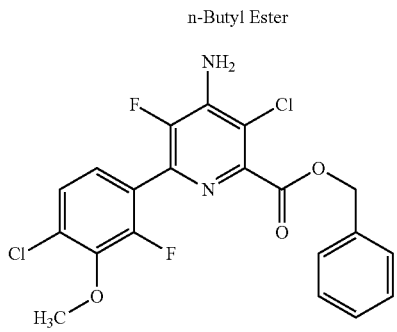

Compound A
Benzyl Ester

Other herbicidal components were applied on an acid equivalent or active ingredient basis and included the 5-enolpyruvylshikimate-3-phosphate synthase (EP SPS)-inhibiting herbicide, glyphosate isopropylamine salt, formulated as Glyphomax®, Durango®, or Rodeo®, glyphosate dimethylamine salt formulated as Durango DMA®, and the glutamine synthase (GS)-inhibiting herbicide, glufosinate ammonium, formulated as Ignite® 280.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 v/v acetone/DMSO to obtain 12× stock solutions, and measured amounts of the formulated compounds can be placed individually in 25 mL glass vials and diluted in a volume of 1.5% (v/v) crop oil concentrate or water to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contain 1.25% (v/v) crop oil concentrate. As required, additional water and/or 97:3 v/v acetone/DMSO can be added to individual application solutions so that the final acetone and DMSO concentrations of the application solutions being compared are 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m$^2$ at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-11.

TABLE 1

Synergistic Activity of Foliar-Applied Compound A Acid and Glyphosate Isopropylamine Salt (Glyphomax ®) Herbicidal Compositions on Control of Weeds Common to Rice Cropping Systems.

| Compound A Acid | Glyphosate isopropylamine salt | Visual Weed Control (%) - 21 DAA | | | |
|---|---|---|---|---|---|
| | | ECHCG | | ECHCO | |
| gae/ha | gae/ha | Obs | Exp | Obs | Exp |
| 4.38 | 0 | 15 | — | 70 | — |
| 8.75 | 0 | 50 | — | 75 | — |
| 0 | 124.5 | 0 | — | 10 | — |
| 0 | 249 | 0 | — | 20 | — |
| 4.38 | 124.5 | 95 | 15 | 90 | 73 |
| 8.75 | 124.5 | 95 | 50 | 95 | 78 |
| 4.38 | 249 | 95 | 15 | 90 | 76 |
| 8.75 | 249 | 95 | 50 | 95 | 80 |

| Compound A Acid | Glyphosate isopropylamine salt | Visual Weed Control (%) - 21 DAA LEFCH | |
|---|---|---|---|
| gae/ha | gae/ha | Obs | Exp |
| 17.5 | 0 | 0 | — |
| 0 | 124.5 | 0 | — |
| 0 | 249 | 45 | — |
| 17.5 | 124.5 | 60 | 0 |
| 17.5 | 249 | 60 | 45 |

| Compound A Acid | Glyphosate isopropylamine salt | Visual Weed Control (%) - 21 DAA CYPDI | |
|---|---|---|---|
| gae/ha | gae/ha | Obs | Exp |
| 4.38 | 0 | 50 | — |
| 0 | 124.5 | 40 | — |
| 0 | 249 | 40 | — |
| 4.38 | 124.5 | 100 | 70 |
| 4.38 | 249 | 85 | 70 |

TABLE 2

Synergistic Activity of Foliar-Applied Compound A Acid and Glyphosate Isopropylamine Salt (Rodeo ®) Herbicidal Compositions on Control of Weeds Common to Rice Cropping Systems.

| Compound A Acid | Glyphosate isopropylamine salt | Visual Weed Control (%) - 21 DAA ECHCO | |
|---|---|---|---|
| gae/ha | gae/ha | Obs | Exp |
| 4.38 | 0 | 60 | — |
| 8.75 | 0 | 90 | — |
| 0 | 105 | 0 | — |
| 0 | 210 | 0 | — |
| 4.38 | 105 | 90 | 60 |
| 8.75 | 105 | 95 | 90 |
| 4.38 | 210 | 95 | 60 |
| 8.75 | 210 | 95 | 90 |

| Compound A Acid | Glyphosate isopropylamine salt | Visual Weed Control (%) - 21 DAA LEFCH | |
|---|---|---|---|
| gae/ha | gae/ha | Obs | Exp |
| 17.5 | 0 | 30 | — |
| 0 | 105 | 25 | — |
| 0 | 210 | 75 | — |
| 0 | 420 | 90 | — |
| 17.5 | 105 | 70 | 48 |
| 17.5 | 210 | 99 | 83 |
| 17.5 | 420 | 95 | 93 |

| Compound A Acid | Glyphosate isopropylamine salt | Visual Weed Control (%) - 21 DAA IPOHE | |
|---|---|---|---|
| gae/ha | gae/ha | Obs | Exp |
| 4.38 | 0 | 10 | — |
| 8.75 | 0 | 35 | — |
| 17.5 | 0 | 45 | — |
| 0 | 105 | 15 | — |
| 0 | 210 | 25 | — |
| 0 | 420 | 55 | — |
| 4.38 | 105 | 50 | 24 |
| 8.75 | 105 | 60 | 45 |
| 17.5 | 105 | 75 | 53 |
| 4.38 | 210 | 75 | 33 |
| 8.75 | 210 | 80 | 51 |
| 17.5 | 210 | 85 | 59 |
| 4.38 | 420 | 65 | 60 |
| 8.75 | 420 | 90 | 71 |
| 17.5 | 420 | 100 | 75 |

TABLE 3

Synergistic Activity of Foliar-Applied Compound A Acid and Glyphosate Isopropylamine Salt (Durango ®) Herbicidal Compositions on Control of Weeds Common to Rice Cropping Systems.

| Compound A Acid | Glyphosate isopropylamine salt | Visual Weed Control (%) - 20 DAA | | | |
|---|---|---|---|---|---|
| | | DIGSA | | LEFCH | |
| gae/ha | gae/ha | Obs | Exp | Obs | Exp |
| 19.4 | 0 | 13 | — | 5 | — |
| 0 | 377 | 10 | — | 88 | — |
| 19.4 | 377 | 45 | 21 | 100 | 88 |

TABLE 4

Synergistic Activity of Foliar-Applied Compound A n-Butyl Ester and Glyphosate Isopropylamine Salt (Durango ®) Herbicidal Compositions on Control of Weeds Common to Rice Cropping Systems.

| Compound A n-Butyl Ester | Glyphosate isopropylamine salt | Visual Weed Control (%) - 20 DAA | | | |
|---|---|---|---|---|---|
| | | ECHCG | | LEFCH | |
| gae/ha | gae/ha | Obs | Exp | Obs | Exp |
| 16 | 0 | 65 | — | 10 | — |
| 0 | 377 | 38 | — | 88 | — |
| 16 | 377 | 90 | 78 | 100 | 89 |

TABLE 5

Synergistic Activity of Foliar-Applied Compound A Benzyl Ester and Glyphosate Isopropylamine Salt (Glyphomax ®) Herbicidal Compositions on Control of Weeds Common to Rice Cropping Systems.

| Compound A Benzyl Ester | Glyphosate isopropylamine salt | Visual Weed Control (%) - 21 DAA | | | |
|---|---|---|---|---|---|
| | | ECHCG | | ECHCO | |
| gae/ha | gae/ha | Obs | Exp | Obs | Exp |
| 4.38 | 0 | 10 | — | 70 | — |
| 8.75 | 0 | 85 | — | 75 | — |
| 0 | 124.5 | 0 | — | 10 | — |
| 0 | 249 | 0 | — | 20 | — |
| 4.38 | 124.5 | 95 | 10 | 95 | 73 |
| 8.75 | 124.5 | 95 | 85 | 95 | 78 |
| 4.38 | 249 | 95 | 10 | 95 | 76 |
| 8.75 | 249 | 90 | 85 | 90 | 80 |

| Compound A Benzyl Ester | Glyphosate isopropylamine salt | Visual Weed Control (%) - 21 DAA LEFCH | |
|---|---|---|---|
| gae/ha | gae/ha | Obs | Exp |
| 4.38 | 0 | 0 | — |
| 8.75 | 0 | 40 | — |
| 17.5 | 0 | 45 | — |
| 0 | 124.5 | 0 | — |
| 4.38 | 124.5 | 20 | 0 |
| 8.75 | 124.5 | 35 | 40 |
| 17.5 | 124.5 | 65 | 45 |

TABLE 6

Synergistic Activity of Foliar-Applied Compound A Benzyl Ester and Glyphosate Isopropylamine Salt (Rodeo ®) Herbicidal Compositions on Control of Weeds Common to Rice Cropping Systems.

| Compound A Benzyl Ester | Glyphosate isopropylamine salt | Visual Weed Control (%) - 21 DAA IPOHE | |
|---|---|---|---|
| gae/ha | gae/ha | Obs | Exp |
| 4.38 | 0 | 10 | — |
| 8.75 | 0 | 10 | — |
| 17.5 | 0 | 25 | — |
| 0 | 105 | 15 | — |
| 0 | 210 | 25 | — |
| 0 | 420 | 55 | — |
| 4.38 | 105 | 20 | 24 |
| 8.75 | 105 | 45 | 24 |
| 17.5 | 105 | 75 | 36 |
| 4.38 | 210 | 65 | 33 |
| 8.75 | 210 | 70 | 33 |
| 17.5 | 210 | 50 | 44 |
| 4.38 | 420 | 85 | 60 |
| 8.75 | 420 | 95 | 60 |
| 17.5 | 420 | 90 | 66 |

TABLE 7

Synergistic Activity of Foliar-Applied Compound A Benzyl Ester and Glyphosate Isopropylamine Salt (Durango ®) Herbicidal Compositions on Control of Weeds Common to Rice Cropping Systems.

| Compound A Benzyl Ester | Glyphosate isopropylamine salt | Visual Weed Control (%) - 20 DAA DIGSA | |
|---|---|---|---|
| gae/ha | gae/ha | Obs | Exp |
| 16 | 0 | 18 | — |
| 0 | 377 | 10 | — |
| 16 | 377 | 53 | 26 |

TABLE 8

Synergistic Activity of Foliar-Applied Compound A Benzyl Ester and Glyphosate Dimethylamine Salt (Durango DMA ®) Herbicidal Compositions on Control of Weeds Common to Rice Cropping Systems.

| Compound A Benzyl Ester | Glyphosate DMA Salt | Visual Weed Control (%) - 21 DAA DIGSA | |
|---|---|---|---|
| gae/ha | gae/ha | Obs | Exp |
| 8 | 0 | 25 | — |
| 16 | 0 | 30 | — |
| 0 | 210 | 75 | — |
| 8 | 210 | 95 | 81 |
| 16 | 210 | 85 | 83 |

| Compound A Benzyl Ester | Glyphosate DMA Salt | Visual Weed Control (%) - 21 DAA IPOHE | |
|---|---|---|---|
| gae/ha | gae/ha | Obs | Exp |
| 8 | 0 | 10 | — |
| 16 | 0 | 10 | — |
| 0 | 105 | 30 | — |
| 8 | 105 | 70 | 37 |
| 16 | 105 | 60 | 37 |

TABLE 9

Synergistic Activity of Foliar-Applied Compound A Acid and Glufosinate Ammonium Herbicidal Compositions on Control of Weeds Common to Rice Cropping Systems.

| Compound A Acid | Glufosinate ammonium salt gae/ha | Visual Weed Control (%) - 21 DAA DIGSA | |
|---|---|---|---|
| | | Obs | Exp |
| 4.38 | 0 | 35 | — |
| 8.75 | 0 | 50 | — |
| 17.5 | 0 | 40 | — |
| 0 | 135.5 | 0 | — |
| 4.38 | 135.5 | 50 | 35 |
| 8.75 | 135.5 | 50 | 50 |
| 17.5 | 135.5 | 55 | 40 |

TABLE 9-continued

Synergistic Activity of Foliar-Applied Compound A Acid and Glufosinate Ammonium Herbicidal Compositions on Control of Weeds Common to Rice Cropping Systems.

| Compound A Acid | Glufosinate ammonium salt | Visual Weed Control (%) - 21 DAA | | | | | |
|---|---|---|---|---|---|---|---|
| | | ECHCG | | ECHCO | | CYPDI | |
| gae/ha | gae/ha | Obs | Exp | Obs | Exp | Obs | Exp |
| 4.38 | 0 | 15 | — | 70 | — | 50 | — |
| 8.75 | 0 | 50 | — | 75 | — | 85 | — |
| 0 | 135.5 | 60 | — | 0 | — | 0 | — |
| 0 | 271 | 10 | — | 0 | — | 0 | — |
| 4.38 | 135.5 | 70 | 66 | 90 | 70 | 80 | 50 |
| 8.75 | 135.5 | 95 | 80 | 90 | 75 | 100 | 85 |
| 4.38 | 271 | 80 | 24 | 95 | 70 | 60 | 50 |
| 8.75 | 271 | 95 | 55 | 95 | 75 | 100 | 85 |

| Compound A Acid | Glufosinate ammonium salt | Visual Weed Control (%) - 21 DAA | |
|---|---|---|---|
| | | LEFCH | |
| gae/ha | gae/ha | Obs | Exp |
| 17.5 | 0 | 0 | — |
| 0 | 135.5 | 0 | — |
| 0 | 271 | 10 | — |
| 17.5 | 135.5 | 15 | 0 |
| 17.5 | 271 | 40 | 10 |

TABLE 10

Synergistic Activity of Foliar-Applied Compound A n-Butyl Ester and Glufosinate Ammonium Herbicidal Compositions on Control of Weeds Common to Rice Cropping Systems.

| Compound A n-Butyl Ester | Glufosinate ammonium salt | Visual Weed Control (%) - 20 DAA IPOHE | |
|---|---|---|---|
| gae/ha | gai/ha | Obs | Exp |
| 16 | 0 | 15 | — |
| 0 | 542 | 50 | — |
| 16 | 542 | 65 | 58 |

TABLE 11

Synergistic Activity of Foliar-Applied Compound A Benzyl Ester and Glufosinate Ammonium Herbicidal Compositions on Control of Weeds Common to Rice Cropping Systems.

| Compound A Benzyl Ester | Glufosinate ammonium salt | Visual Weed Control (%) - 21 DAA | | | |
|---|---|---|---|---|---|
| | | ECHCG | | ECHCO | |
| gae/ha | gae/ha | Obs | Exp | Obs | Exp |
| 4.38 | 0 | 10 | — | 70 | — |
| 8.75 | 0 | 85 | — | 75 | — |
| 0 | 135.5 | 60 | — | 0 | — |
| 0 | 271 | 10 | — | 0 | — |
| 4.38 | 135.5 | 90 | 64 | 95 | 70 |
| 8.75 | 135.5 | 95 | 94 | 95 | 75 |
| 4.38 | 271 | 90 | 19 | 70 | 70 |
| 8.75 | 271 | 90 | 87 | 90 | 75 |

TABLE 11-continued

Synergistic Activity of Foliar-Applied Compound A Benzyl Ester and Glufosinate Ammonium Herbicidal Compositions on Control of Weeds Common to Rice Cropping Systems.

| Compound A Benzyl Ester | Glufosinate ammonium salt | Visual Weed Control (%) - 20 DAA IPOHE | |
|---|---|---|---|
| gae/ha | gai/ha | Obs | Exp |
| 16 | 0 | 18 | — |
| 0 | 542 | 50 | — |
| 16 | 542 | 80 | 59 |

| Compound A Benzyl Ester | Glufosinate ammonium salt | Visual Weed Control (%) -21 DAA IPOHE | |
|---|---|---|---|
| gae/ha | gai/ha | Obs | Exp |
| 8 | 0 | 10 | — |
| 16 | 0 | 10 | — |
| 32 | 0 | 45 | — |
| 0 | 112.5 | 10 | — |
| 8 | 112.5 | 20 | 19 |
| 16 | 112.5 | 65 | 19 |
| 32 | 112.5 | 65 | 51 |

| | | |
|---|---|---|
| CYPDI | *Cyperus difformis* L. | sedge, small-flower umbrella |
| DIGSA | *Digitaria sanguinalis* (L.) Scop. | crabgrass, large |
| ECHCG | *Echinochloa crusgalli* (L.) Beauv. | barnyardgrass |
| ECHCO | *Echinochloa colona* (L.) Link | junglerice |
| IPOHE | *Ipomoea hederacea* Jacq. | morningglory, ivyleaf |
| LEFCH | *Leptochloa chinensis* (L.) Nees | sprangletop, Chinese | gae/ha = grams acid equivalent per hectare
gai/ha = grams active ingredient per hectare
Obs = observed value
Exp = expected value as calculated by Colby's equation
DAA = days after application Example II Evaluation of In-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters ($cm^2$) leaving a headspace of 3 centimeters (cm) in each pot. Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 840 mL of mud contained in 32-oz. non-perforated plastic pots with a surface area of 86.59 $cm^2$ 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 hr photoperiod which was maintained at about 29'C during the day and 26° C. during the night. Nutrients were added as Osmocote® (19:6:12, N:P:K+minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)pyridine-2-carboxylic acid (compound A) each formulated as an SC (suspension concentrate) and various herbicidal components alone and in combination. Forms of compound A were applied on an acid equivalent basis.

Forms of compound A (compound of formula I) tested include:

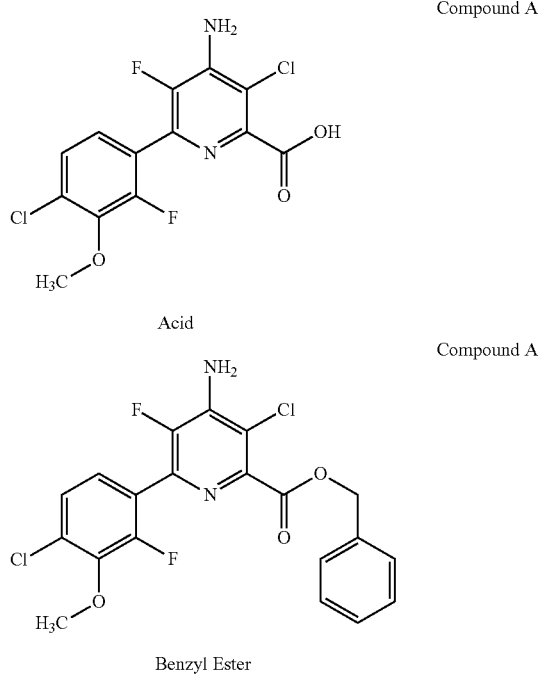

Acid

Compound A

Benzyl Ester

Other herbicidal components were applied on an acid equivalent or active ingredient basis and included the 5-enolpyruvylshikimate-3-phosphate synthase (EPSPS)-inhibiting herbicide, glyphosate isopropylamine salt, formulated as Rodeo®.

Treatment requirements for each compound or herbicidal component were calculated based upon the rates being tested, the concentration of active ingredient or acid equivalent in the formulation, an application volume of 2 mL per component per pot, and an application area of 86.59 cm² per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount can be placed in an individual 100 to 200 mL glass vial and dissolved in a volume of acetone to obtain concentrated stock solutions. If the test compound does not dissolve readily, the mixture can be warmed and/or sonicated. The concentrated stock solutions obtained can be diluted with an equivalent volume of an aqueous mixture containing 2.5% (v/v) crop oil concentrate so that the final application solutions contain 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 12.

TABLE 12

Synergistic Activity of In-Water Applications of Compound A Acid and Glyphosate Isopropylamine Salt Herbicidal Compositions on Control of Weeds Common to Rice Cropping Systems.

| Compound A Acid | Glyphosate Isopropylamine Salt | Visual Weed Control (%) - 21 DAA SCPMA | |
|---|---|---|---|
| gae/ha | gae/ha | Obs | Exp |
| 8.75 | 0 | 0 | — |
| 17.5 | 0 | 0 | — |
| 35 | 0 | 0 | — |
| 0 | 210 | 0 | — |
| 0 | 420 | 0 | — |
| 8.75 | 210 | 0 | 0 |
| 17.5 | 210 | 0 | 0 |
| 35 | 210 | 100 | 0 |
| 8.75 | 420 | 100 | 0 |
| 17.5 | 420 | 100 | 0 |
| 35 | 420 | 90 | 0 |

SCPMA *Schoenoplectus maritimus* (L.) Lye or
*Bolboschoenus maritimus* (L.) Palla clubrush, sea
gae/ha = grams acid equivalent per hectare
gai/ha = grams active ingredient per hectare
Obs = observed value
Exp = expected value as calculated by Colby's equation
DAA = days after application

Example III

Evaluation of Postemergence Foliar-Applied Herbicidal Mixtures for Control of Weeds Common to Row Crops such as Corn and Soybeans Seeds or nutlets of the desired test plant species were planted in a soil matrix prepared by mixing a loam or sandy loam soil (e.g., 43 percent silt, 19 percent clay, and 38 percent sand, with a pH of about 8.1 and an organic matter content of about 1.5 percent) and calcareous grit in an 80 to 20 ratio. The soil matrix was contained in plastic pots with a surface area of 84.6 square centimters ($cm^2$) and a volume of 560 cubic centimeters ($cm^3$). When required to ensure good germination and healthy plants, a fungicide treatment and/or other chemical or physical treatment was applied. The plants were grown for 7-31 days (d) in a greenhouse with an approximate 15 hour (h) photoperiod which was maintained at about 23-29° C. during the day and 22-28° C. during the night. Nutrients (Peters Excel® 15-5-15 5-Ca 2-Mg) and water were added on a regular basis and supplemental lighting was provided with overhead metal halide 1000-Watt lamps as necessary. The plants were employed for testing when they reached the first, second, or third true leaf stage.

Treatment requirements were calculated based upon the rates being tested, the concentration of active ingredient or acid equivalent in the formulation, and a 12 mL application volume at a rate of 187 L/ha.

Treatments consisted of the acid or esters of 4-amino-3-chloro-5-fluoro-6-(4-chloro-2-fluoro-3-methoxy-phenyl)pyridine-2-carboxylic acid (Compound A), each formulated as an SC (suspension concentrate), and various herbicidal components alone and in combination. Forms of compound A were applied on an acid equivalent basis.

Forms of compound A (compound of formula I) tested include:

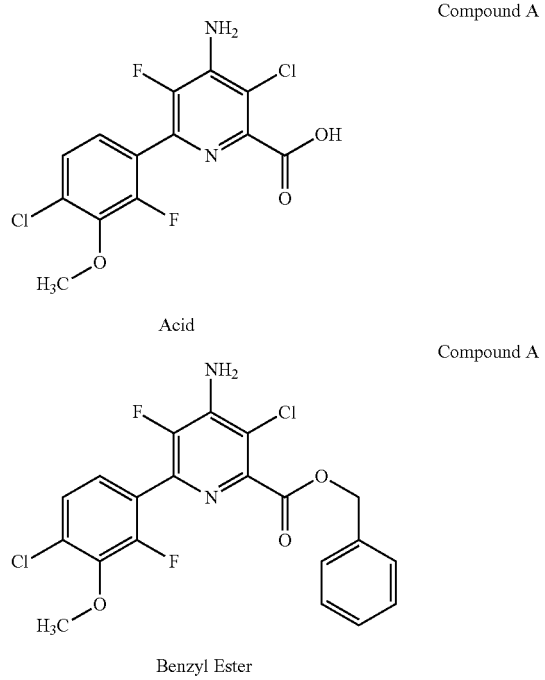

Compound A
Acid

Compound A
Benzyl Ester

Other herbicidal components were applied on an acid equivalent or active ingredient basis and included the 5-enolpyruvylshikimate-3-phosphate synthase (EPSPS)-inhibiting herbicide, glyphosate dimethylamine salt, formulated as Durango DMA® and the glutamine synthase (GS)-inhibiting herbicide, glufosinate ammonium, formulated as Ignite® 280.

For treatments comprised of formulated compounds, measured amounts of compounds were placed individually in 25 mL glass vials and diluted in a volume of 1.5% (v/v) Agridex® crop oil concentrate to obtain 6× stock solutions. If a test compound did not dissolve readily, the mixture was warmed and/or sonicated. Application solutions were prepared by adding an appropriate amount of each stock solution (typically 2 mL) and diluted to the appropriate final concentrations with the addition of an aqueous mixture of 1.5% (v/v) crop oil concentrate and water so that the final spray solutions contained 1.25% (v/v) crop oil concentrate.

For treatments comprised of technical compounds, weighed amounts can be placed individually in 25 mL glass vials and dissolved in a volume of 97:3 v/v acetone/DMSO to obtain 6× stock solutions. If a test compound does not dissolve readily, the mixture can be warmed and/or sonicated. Application solutions can be prepared by adding an appropriate amount of each stock solution (e.g., 2 mL) and diluted to the appropriate final concentrations with the addition of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 v/v acetone/DMSO to obtain 6× stock solutions, and measured amounts of the formulated compounds can be placed individually in 25 mL glass vials and diluted in a volume of 1.5% (v/v) crop oil concentrate or water to obtain 6× stock solutions. If a test compound does not dissolve readily, the mixture can be warmed and/or sonicated. Application solutions can be prepared by adding an appropriate amount of each stock solution (e.g., 2 mL) and diluted to the appropriate final concentrations with the addition of an appropriate amount of an aqueous mixture of 1.5% (v/v) crop oil concentrate so that the final spray solutions contain 1.25% (v/v) crop oil concentrate. When required, additional water and/or 97:3 v/v acetone/DMSO can be added to individual application solutions so that the final acetone and DMSO concentrations of the application solutions being compared are 8.1% and 0.25%, respectively.

All stock solutions and applications solutions were visually inspected for compound compatibility prior to application. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters ($m^2$) at a spray height of 18 to 20 inches (46 to 50 cm) above the average plant canopy height. Control plants were sprayed in the same manner with the solvent blank.

The treated plants and control plants were placed in a greenhouse as described above and watered by sub-irrigation to prevent wash-off of the test compounds. After approximately 2 weeks, the condition of the test plants as compared with that of the untreated plants was determined visually and scored on a scale of 0 to 100 percent where 0 corresponds to no injury or growth inhibition and 100 corresponds to complete kill.

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 13-15.

TABLE 13

Synergistic Activity of Foliar-Applied Compound A Acid and Glyphosate Dimethylamine Salt (Durango DMA ®) Herbicidal Compositions on Control of Weeds Common to Row Crops such as Corn and Soybean Cropping Systems.

| Compound A Acid | Glyphosate dimethylamine salt | Visual Weed Control (%) - 16 DAA SORHA | |
|---|---|---|---|
| gae/ha | gae/ha | Obs | Exp |
| 3.75 | 0 | 0 | — |
| 0 | 105 | 0 | — |
| 0 | 210 | 10 | — |
| 0 | 420 | 25 | — |
| 3.75 | 105 | 0 | 0 |
| 3.75 | 210 | 40 | 10 |
| 3.75 | 420 | 45 | 25 |

TABLE 14

Synergistic Activity of Foliar-Applied Compound A Acid and Glufosinate Ammonium Herbicidal Compositions on Control of Weeds Common to Row Crops such as Corn and Soybean Cropping Systems.

| Compound A Acid | Glufosinate ammonium salt | Visual Weed Control (%) - 16 DAA AVEFA | |
|---|---|---|---|
| gae/ha | gae/ha | Obs | Exp |
| 3.75 | 0 | 0 | — |
| 7.5 | 0 | 0 | — |
| 15 | 0 | 10 | — |
| 0 | 28.25 | 0 | — |
| 0 | 56.5 | 0 | — |
| 3.75 | 28.25 | 0 | 0 |
| 7.5 | 28.25 | 15 | 0 |
| 15 | 28.25 | 20 | 10 |
| 3.75 | 56.5 | 20 | 0 |
| 7.5 | 56.5 | 20 | 0 |
| 15 | 56.5 | 10 | 10 |

| Compound A Acid | Glufosinate ammonium salt | Visual Weed Control (%) - 16 DAA ELEIN | |
|---|---|---|---|
| gae/ha | gae/ha | Obs | Exp |
| 7.5 | 0 | 10 | — |
| 15 | 0 | 10 | — |
| 0 | 28.25 | 0 | — |
| 0 | 56.5 | 0 | — |
| 0 | 113 | 10 | — |
| 7.5 | 28.25 | 25 | 10 |
| 15 | 28.25 | 10 | 10 |
| 7.5 | 56.5 | 35 | 10 |
| 15 | 56.5 | 30 | 10 |
| 7.5 | 113 | 40 | 19 |
| 15 | 113 | 45 | 19 |

| Compound A Acid | Glufosinate ammonium salt | Visual Weed Control (%) - 13 DAA SORHA | |
|---|---|---|---|
| gae/ha | gae/ha | Obs | Exp |
| 3.75 | 0 | 0 | — |
| 7.5 | 0 | 0 | — |
| 15 | 0 | 0 | — |
| 0 | 271 | 20 | — |
| 0 | 542 | 25 | — |
| 3.75 | 271 | 25 | 20 |
| 7.5 | 271 | 40 | 20 |
| 15 | 271 | 40 | 20 |
| 3.75 | 542 | 40 | 25 |
| 7.5 | 542 | 90 | 25 |
| 15 | 542 | 40 | 25 |

TABLE 15

Synergistic Activity of Foliar-Applied Compound A Benzyl Ester and Glufosinate Ammonium Herbicidal Compositions on Control of Weeds Common to Row Crops such as Corn and Soybean Cropping Systems.

| Compound A Benzyl Ester | Glufosinate ammonium salt | Visual Weed Control (%) - 13 DAA SORHA | |
|---|---|---|---|
| gae/ha | gae/ha | Obs | Exp |
| 3.75 | 0 | 0 | — |
| 7.5 | 0 | 0 | — |
| 15 | 0 | 10 | — |
| 0 | 271 | 20 | — |
| 0 | 542 | 25 | — |
| 3.75 | 271 | 20 | 20 |
| 7.5 | 271 | 40 | 20 |
| 15 | 271 | 30 | 28 |
| 3.75 | 542 | 60 | 25 |
| 7.5 | 542 | 45 | 25 |
| 15 | 542 | 60 | 33 |

AVEFA  *Avena fatua* L.  oat, wild
ELEIN  *Eleusine indica* (L.)  Gaertn. goosegrass
SORHA  *Sorghum halepense* (L.)  Pers. johnsongrass
gae/ha = grams acid equivalent per hectare
gai/ha = grams active ingredient per hectare
Obs = observed value
Exp = expected value as calculated by Colby's equation
DAA = days after application

Example IV

Evaluation of Postemergence Foliar-Applied Herbicidal Mixtures for General Weed Control Seeds or nutlets of the desired test plant species were planted in Sun Gro Metro-Mix® 360 planting mixture, which typically has a pH of 6.0 to 6.8 and an organic matter content of about 30 percent, in plastic pots with a surface area of 84.6 square centimeters ($cm^2$). When required to ensure good germination and healthy plants, a fungicide treatment and/or other chemical or physical treatment was applied. The plants were grown for 7-31 days (d) in a greenhouse with an approximate 15 hour (h) photoperiod which was maintained at about 23-29° C. during the day and 22-28° C. during the night. Nutrients (Peters Excel® 15-5-15 5-Ca 2-Mg) and water were added on a regular basis and supplemental lighting was provided with overhead metal halide 1000-Watt lamps as necessary. The plants were employed for testing when they reached the first, second, or third true leaf stage.

Treatment requirements were calculated based upon the rates being tested, the concentration of active ingredient or acid equivalent in the formulation, and a 12 mL application volume at a rate of 187 L/ha.

Treatments consisted of the acid or the benzyl ester of 4-amino-3-chloro-5-fluoro-6-(4-chloro-2-fluoro-3-methoxy-phenyl)pyridine-2-carboxylic acid (Compound A), each formulated as an SC, and various herbicidal components alone and in combination. Forms of compound A were applied on an acid equivalent basis.

Forms of compound A (compound of formula I) tested include:

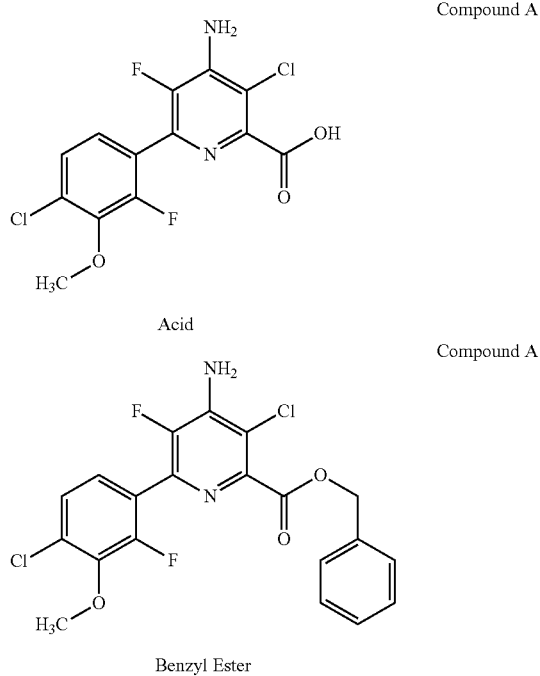

Compound A
Acid

Compound A
Benzyl Ester

Other herbicidal components were applied on an acid equivalent or active ingredient basis and included the 5-enolpyruvylshikimate-3-phosphate synthase (EPSPS)-inhibiting herbicide, glyphosate dimethylamine salt, formulated as Durango DMA® and the glutamine synthase (GS)-inhibiting herbicide, glufosinate ammonium, formulated as Ignite® 280.

For treatments comprised of formulated compounds, measured amounts of compounds were placed individually in 25 mL glass vials and diluted in a volume of 1.25% (v/v) Agri-dex crop oil concentrated to obtain 12× stock solutions. If a test compound did not dissolve readily, the mixture was warmed and/or sonicated. Application solutions were prepared by adding an appropriate amount of each stock solution (typically 1 mL) and diluted to the appropriate final concentrations with the addition of 10 mL of an aqueous mixture of 1.25% (v/v) Agri-dex crop oil concentrate so that the final spray solutions contained 1.25% (v/v) Agri-dex crop oil concentrate.

All stock solutions and applications solutions were visually inspected for compound compatibility prior to application. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters ($m^2$) at a spray height of 18 to 20 inches (46 to 50 cm) above the average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 16-17.

TABLE 16

Synergistic Activity of Foliar-Applied Compound A Benzyl Ester and Glyphosate Dimethylamine Salt (Durango DMA ®) Herbicidal Compositions for General Weed Control.

| Compound A Benzyl Ester | Glyphosate DMA salt | Visual Weed Control (%) - 18 DAA | | | |
|---|---|---|---|---|---|
| | | VIOTR | | SETFA | |
| gae/ha | gae/ha | Obs | Exp | Obs | Exp |
| 2 | 0 | 15 | — | 40 | — |
| 4 | 0 | 20 | — | 40 | — |
| 0 | 210 | 60 | — | 10 | — |
| 0 | 420 | 85 | — | 90 | — |
| 2 | 210 | 70 | 66 | 90 | 46 |
| 4 | 210 | 80 | 68 | 90 | 46 |
| 2 | 420 | 95 | 87 | 95 | 94 |
| 4 | 420 | 100 | 88 | 99 | 94 |

| Compound A Benzyl Ester | Glyphosate DMA salt | Visual Weed Control (%) -18 DAA CHEAL | |
|---|---|---|---|
| gae/ha | gae/ha | Obs | Exp |
| 2 | 0 | 50 | — |
| 4 | 0 | 70 | — |
| 8 | 0 | 90 | — |
| 16 | 0 | 95 | — |

TABLE 16-continued

Synergistic Activity of Foliar-Applied Compound A Benzyl Ester and Glyphosate Dimethylamine Salt (Durango DMA ®) Herbicidal Compositions for General Weed Control.

| | | | |
|---|---|---|---|
| 32 | 0 | 99 | — |
| 0 | 420 | 0 | — |
| 0 | 840 | 30 | — |
| 2 | 420 | 90 | 50 |
| 4 | 420 | 100 | 70 |
| 8 | 420 | 90 | 90 |
| 16 | 420 | 100 | 95 |
| 32 | 420 | 100 | 99 |
| 2 | 840 | 100 | 65 |
| 4 | 840 | 99 | 79 |
| 8 | 840 | 95 | 93 |
| 16 | 840 | 100 | 97 |
| 32 | 840 | 100 | 99 |

| Compound A Benzyl Ester | Glyphosate DMA salt | Visual Weed Control (%) -18 DAA DIGSA | |
|---|---|---|---|
| gae/ha | gae/ha | Obs | Exp |
| 2 | 0 | 0 | — |
| 4 | 0 | 0 | — |
| 8 | 0 | 0 | — |
| 16 | 0 | 0 | — |
| 32 | 0 | 30 | — |
| 0 | 210 | 40 | — |
| 2 | 210 | 70 | 40 |
| 4 | 210 | 75 | 40 |
| 8 | 210 | 75 | 40 |
| 16 | 210 | 65 | 40 |
| 32 | 210 | 85 | 58 |

| Compound A Benzyl Ester | Glyphosate DMA salt | Visual Weed Control (%) -18 DAA CYPES | |
|---|---|---|---|
| gae/ha | gae/ha | Obs | Exp |
| 2 | 0 | 40 | — |
| 0 | 420 | 40 | — |
| 0 | 840 | 70 | — |
| 2 | 420 | 100 | 64 |
| 2 | 840 | 100 | 82 |

TABLE 17

Synergistic Activity of Foliar-Applied Compound A Benzyl Ester and Glufosinate Ammonium Herbicidal Compositions for General Weed Control.

| Compound A Benzyl Ester | Glufosinate ammonium salt | Visual Weed Control (%) - 18 DAA | | | | | |
|---|---|---|---|---|---|---|---|
| | | CIRAR | | DIGSA | | AMARE | |
| gae/ha | gai/ha | Obs | Exp | Obs | Exp | Obs | Exp |
| 2 | 0 | 60 | — | 0 | — | 50 | — |
| 4 | 0 | 70 | — | 0 | — | 60 | — |
| 8 | 0 | 80 | — | 0 | — | 85 | — |
| 16 | 0 | 85 | — | 0 | — | 85 | — |
| 32 | 0 | 90 | — | 30 | — | 100 | — |
| 0 | 225 | 15 | — | 25 | — | 50 | — |
| 2 | 225 | 75 | 66 | 30 | 25 | 95 | 75 |
| 4 | 225 | 95 | 75 | 45 | 25 | 99 | 80 |
| 8 | 225 | 100 | 83 | 40 | 25 | 85 | 93 |
| 16 | 225 | 100 | 87 | 60 | 25 | 85 | 93 |
| 32 | 225 | 80 | 92 | 60 | 48 | 99 | 100 |

TABLE 17-continued

Synergistic Activity of Foliar-Applied Compound A Benzyl Ester and Glufosinate Ammonium Herbicidal Compositions for General Weed Control.

| Compound A Benzyl Ester | Glufosinate ammonium salt | Visual Weed Control (%) - 18 DAA IPOHE | |
|---|---|---|---|
| gae/ha | gai/ha | Obs | Exp |
| 2 | 0 | 15 | — |
| 4 | 0 | 25 | — |
| 8 | 0 | 25 | — |
| 16 | 0 | 35 | — |
| 32 | 0 | 45 | — |
| 0 | 112.5 | 10 | — |
| 0 | 225 | 20 | — |
| 0 | 450 | 50 | — |
| 2 | 112.5 | 20 | 24 |
| 4 | 112.5 | 80 | 33 |
| 8 | 112.5 | 40 | 33 |
| 16 | 112.5 | 40 | 42 |
| 32 | 112.5 | 80 | 51 |
| 2 | 225 | 60 | 32 |
| 4 | 225 | 55 | 40 |
| 8 | 225 | 40 | 40 |
| 16 | 225 | 60 | 48 |
| 32 | 225 | 60 | 56 |
| 2 | 450 | 100 | 58 |
| 4 | 450 | 60 | 63 |
| 8 | 450 | 100 | 63 |
| 16 | 450 | 100 | 68 |
| 32 | 450 | 100 | 73 |

| Compound A Benzyl Ester | Glufosinate ammonium salt | Visual Weed Control (%) - 18 DAA | | | |
|---|---|---|---|---|---|
| | | CHEAL | | CYPES | |
| gae/ha | gai/ha | Obs | Exp | Obs | Exp |
| 2 | 0 | 50 | — | 40 | — |
| 4 | 0 | 70 | — | 75 | — |
| 8 | 0 | 90 | — | 80 | — |
| 0 | 112.5 | 0 | — | 0 | — |
| 0 | 225 | 10 | — | 0 | — |
| 0 | 450 | 30 | — | 0 | — |
| 2 | 112.5 | 90 | 50 | 50 | 40 |
| 4 | 112.5 | 95 | 70 | 95 | 75 |
| 8 | 112.5 | 95 | 90 | 95 | 80 |
| 2 | 225 | 85 | 55 | 30 | 40 |
| 4 | 225 | 99 | 73 | 85 | 75 |
| 8 | 225 | 100 | 91 | 95 | 80 |
| 2 | 450 | 90 | 65 | 40 | 40 |
| 4 | 450 | 100 | 79 | 90 | 75 |
| 8 | 450 | 99 | 93 | 95 | 80 |

| Compound A Benzyl Ester | Glufosinate ammonium salt | Visual Weed Control (%) - 18 DAA SETFA | |
|---|---|---|---|
| gae/ha | gai/ha | Obs | Exp |
| 2 | 0 | 40 | — |
| 4 | 0 | 40 | — |
| 8 | 0 | 75 | — |
| 16 | 0 | 85 | — |
| 32 | 0 | 90 | — |
| 0 | 450 | 60 | — |
| 2 | 450 | 99 | 76 |
| 4 | 450 | 100 | 76 |
| 8 | 450 | 100 | 90 |

TABLE 17-continued

Synergistic Activity of Foliar-Applied
Compound A Benzyl Ester and Glufosinate Ammonium
Herbicidal Compositions for General Weed Control.

| 16 | 450 | 99 | 94 |
| 32 | 450 | 100 | 96 |

| Compound A Benzyl Ester | Glufosinate ammonium salt | Visual Weed Control (%) - 18 DAA ECHCG | |
|---|---|---|---|
| gae/ha | gai/ha | Obs | Exp |
| 8 | 0 | 40 | — |
| 0 | 112.5 | 0 | — |
| 0 | 225 | 0 | — |
| 0 | 450 | 10 | — |
| 8 | 112.5 | 90 | 40 |
| 8 | 225 | 90 | 40 |
| 8 | 450 | 85 | 46 |

AMARE *Amaranthus retroflexus* L. pigweed, redroot
CHEAL *Chenopodium album* L. lambsquarters, common
CIRAR *Cirsium arvense* (L.) Scop. thistle, Canada
CYPES *Cyperus esculentus* L. nutsedge, yellow
DIGSA *Digitaria sanguinalis* (L.) Scop. crabgrass, large
ECHCG *Echinochloa crusgalli* (L.) Beauv. barnyardgrass
IPOHE *Ipomoea hederacea* Jacq. morning glory, ivyleaf
SETFA *Setaria faberi* Herrm. foxtail, giant
VIOTR *Viola tricolor* L. pansy
gae/ha = grams acid equivalent per hectare
gai/ha = grams active ingredient per hectare
Obs = observed value
Exp = expected value as calculated by Colby's equation
DAA = days after application

What is claimed is:

1. A herbicidal composition comprising a herbicidally effective amount of (a) a compound of the formula (I):

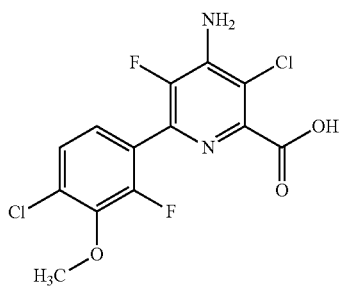

(I)

or an agriculturally acceptable salt or alkyl ester or benzyl ester thereof and (b) glufosinate-ammonium, glyphosate dimethylammonium, glyphosate isopropylammonium, glyphosate trimesium, glufosinate or glyphosate, or a salt or ester thereof wherein (a) and (b) are present in the composition in a ratio such that the composition exhibits herbicidal synergy.

2. The composition of claim 1, wherein (a) is a benzyl ester of compound (I).

3. The composition of claim 1, wherein (a) is a carboxylic acid of the compound of formula (I).

4. The composition of claim 1, wherein (a) is a $C_{1-4}$ alkyl ester of the compound of formula (I).

5. The composition of claim 1, further comprising a herbicide safener, carrier and/or adjuvant.

6. The composition of claim 1, wherein the weight ratio of the compound of formula (I) or agriculturally acceptable salt or ester thereof to glufosinate-ammonium is from about 1:780 to about 1:1.

7. The composition of claim 1, wherein the weight ratio of the compound of formula (I) or agriculturally acceptable salt or ester thereof to glyphosate dimethylammonium is from about 1:1120 to about 1:4.

8. The composition of claim 1, wherein the weight ratio of the compound of formula (I) or agriculturally acceptable salt or ester thereof to glyphosate isopropylammonium is from about 1:210 to about 1:3.

9. The composition of claim 1, wherein the weight ratio of the compound of formula (I) or agriculturally acceptable salt or ester thereof to glyphosate trimesium is from about 1:852 to about 1:1.

10. The composition of claim 1, wherein the weight ratio of the compound of formula (I) or agriculturally acceptable salt or ester thereof to glyphosate is from about 1:1120 to about 1:1.

11. A method of controlling undesirable vegetation which comprises contacting the vegetation or the locus thereof with, or applying to the soil or water to prevent the emergence or growth of vegetation, a combination comprising (a) a compound of the formula (I);

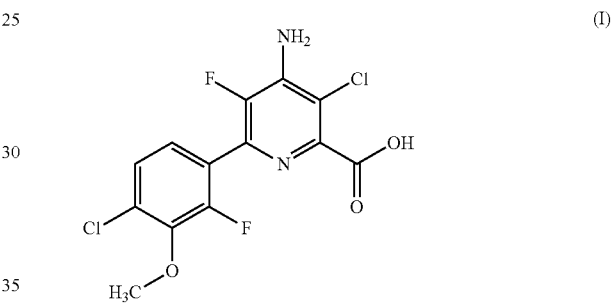

(I)

or an agriculturally acceptable salt or ester thereof and (b) a compound selected from: glufosinate ammonium, glyphosate dimethylammonium, glyphosate isopropylammonium, glyphosate trimesium, glufosinate and glyphosate, or a salt thereof wherein (a) and (b) are present in the combination in a ratio such that the combination exhibits herbicidal synergy wherein the undesirable vegetation is controlled in direct-seeded, water-seeded and transplanted rice, cereals, wheat, barley, oats, rye, sorghum, maize, pastures, grasslands, rangelands, fallowland and turf.

12. The method of claim 11, wherein the locus is water in a flooded rice paddy.

13. The method of claim 11, wherein the (a) and (b) are applied pre-emergently and/or post emergently to the undersirable vegetation or the crop.

14. The method of claim 11, wherein the undesirable vegetation is controlled in glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitor-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, long chain fatty acid inhibitor-, fatty acid and lipid biosynthesis inhibitor-, photosystem I inhibitor-, photosystem II inhibitor-, triazine-, or bromoxynil-tolerant crops.

15. The method of claim 14, wherein the tolerant crop possesses multiple or stacked traits conferring tolerance to multiple herbicides.

16. The method of claim 11, wherein the undesirable vegetation comprises a herbicide resistant or tolerant plant.

17. The method of claim 16, wherein the resistant or tolerant plant is resistant and tolerant to multiple herbicides.

18. The method of claim 17, wherein the resistant or tolerant plant is resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid synthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *

UNITED STATES PATENT AND TRADEMARK OFFICE
CERTIFICATE OF CORRECTION

| | |
|---|---|
| PATENT NO. | : 8,895,470 B2 |
| APPLICATION NO. | : 13/836653 |
| DATED | : November 25, 2014 |
| INVENTOR(S) | : Carla N. Yerkes et al. |

It is certified that error appears in the above-identified patent and that said Letters Patent is hereby corrected as shown below:

In the Claims

Claim 13, Column 44, Lines 51-52 correct the text as follows:

undesirable

Signed and Sealed this
Seventh Day of April, 2015

Michelle K. Lee
*Director of the United States Patent and Trademark Office*